US00PP07816P

United States Patent [19]

Carrier et al.

[11] Patent Number: Plant 7,816

[45] Date of Patent: Mar. 3, 1992

[54] ALSTROEMERIA NAMED GALENA

[75] Inventors: Leonard E. Carrier, Encinitas, Calif.; Stephen Garton, West Jordan, Utah

[73] Assignee: Native Plants, Incorporated, Salt Lake City, Utah

[21] Appl. No.: 512,160

[22] Filed: Apr. 20, 1990

[51] Int. Cl.[5] ..... A01H 5/00

[52] U.S. Cl. ..... Plt./68

[58] Field of Search ..... Plt./68

*Primary Examiner*—Howard J. Locker

*Attorney, Agent, or Firm*—Venable, Baetjer, Howard & Civiletti

[57] ABSTRACT

This plant is particularly characterized by its dwarf habit which makes the plant eminently suitable for cultivation as a potted plant. In addition, the plant bears several flowering stalks which carry large attractive flowers which are predominantly of a red-violet coloration. The attractive flowers and desirable growth habit of this new plant provides a novel addition to the range of Alstroemerias.

1 Drawing Sheet

BACKGROUND OF THE NEW PLANT

This new variety of Alstroemeria originated as a seedling resulting from crossing two plants growing among a collection of breeding stock maintained in a greenhouse in Encinitas, Calif. The seedling was selected for further propagation and testing because of the dwarf characteristic of the whole plant, and the attractive color of the many large flowers contained in several inflorescences as the plant bloomed in a pot. The select plant was propagated in Salt Lake City, Utah by division of the rhizomatous rootstock and through tissue culture. The distinguishing characteristics of the new plant hold true in successive vegetative generations and appear to be firmly fixed. Propagation work is currently being carried out in Salt Lake City using tissue culture methods.

DESCRIPTION OF THE DRAWING

This new variety of Alstroemeria plant is illustrated by the accompnaying photographic drawing in full color showing a blooming umbel of the plant with buds and flowers in different stages of flower development. The color renditions are believed to be as close to the specified color as is possible to obtain by conventional photographic procedures.

DESCRIPTION OF THE NEW PLANT

The following is a detailed description of the new Alstroemeria variety with color designations according to The R.H.S. Colour Chart of The Royal Horticultural Society of London, England. The observations were made on plants grown in a greenhouse in Utah county, Utah, during the summer.

THE PLANT

Origin: Seedling (73-LAV-77A).

Parentage:

*Seed parent.*—Breeding stock plant No. LAV.

*Pollen parent.*—Breeding stock plant No. 77A.

Classification: Alstroemeria hybrid.

Form: Compact, erect bush with a slightly spreading habit having several flower stalks bearing branches with simple umbel arrangement at the tops.

Height: About 35 to 50 cm.

Growth: Erect, vigorous, and compact.

Rootstock: Rhizomatous, the rhizomes bear numerous buds which give rise to vegetative and reproductive shoots throughout the growth period. Rhizomes also produce roots, some of which become tuberous.

Foliage:

*Quantity.*—Medium, about 25 to 30 leaves per stem.

*Leaf size.*—About 10 cm.

*Leaf shape.*—Elliptical.

*Texture.*—Waxy.

*Color.*—Upper surface — Dark green, Lower surface — Grey-green.

THE BUD

Form: Pear-shaped. The six petals are perianth and there is no calyx.

Size: Medium.

*Diameter.*—1.0 cm.

*Length.*—1.8 cm.

Length of peduncle: 1.5 to 2.5 cm.

THE FLOWER

Blooming habit: Continuous and freely flowering throughout the season.

Flower size: Large.

*Diameter.*—About 6.5 cm.

*Length.*—About 6.0 cm.

Shape: Generally funnel-like.

Borne: Singly.

Petalage:

*Number.*—Six.

*Arrangement.*—Two concentric circles of three.

*Form.*—Outer petals — Obcordate, Inner petals — Elliptical.

*Texture.*—Smooth.

*Appearance.*—Satiny.

*Color.*—Outer Petals: The general color is red-purple, 74D, with a darker patch 74C in the middle of the distal half. There is a green tip, 137A, in the middle of the distal margin. The reverse surface is red-purple, 74D, with three green veins visible on the distal part originating from the protruberance. Proximal to the veins is an area of darker color, 74C. Inner petals: Upper: There is a small green tip which protrudes from the middle of the distal margin. The distal red-purple part, 74D, is subtended by a white area with a central yellow patch, 7C. The base is red-purple, 74D. Longitudinal greyed-purple streaks, 187A, are prominent on the basal and middle portions. The distal portion of the reverse surface is red-purple, 74D. The base is 74D. Centrally, there is a green-yellow patch, 1B. Streaks on the other surface are visible through the petal. Lower: Longitudinal, greyed-purple streaks, 187A, are visible on the distal half. The petal is red-purple, 74D, with a darker patch, 74C, central. There is a small green tip which extends from the middle of the distal margin. The general color of the reverse surface is red-purple, 74D, with a patch of darker color central, 74C. Streaks on the other surface are visible through the petal.

Persistence: The flowers hang and dry.

Lasting quality: On the plant, 14–18 days.

Main stem or stalk:

*Length.*—45 to 55 cm.

*Color.*—Green.

*Character.*—Upright, strong and thick.

REPRODUCTIVE ORGANS

Stamens:

*Number.*—Six.

*Arrangement.*—One opposite each petal.

*Anthers.*—Size: 6.0 mm. Color — Beige.

*Filaments.*—Length: About 4.0 cm. Color: Purple-pink.

*Pollen.*—Color: Grey-blue.

Pistils:

*Number.*—One.

*Style.*—Length: About 4.0 cm. Color: Purple-pink.

*Stigma.*—Color: Pink.

Fruit:

*Shape.*—Capsular.

*Color.*—Light brown at maturity.

What is claimed:

1. A new and distinctive Alstroemeria hybrid, substantially as shown and described herein, characterized by a dwarf habit and large predominantly red-violet colored flowers which are borne in attractive inflorescences on relatively dwarf flower stalks.

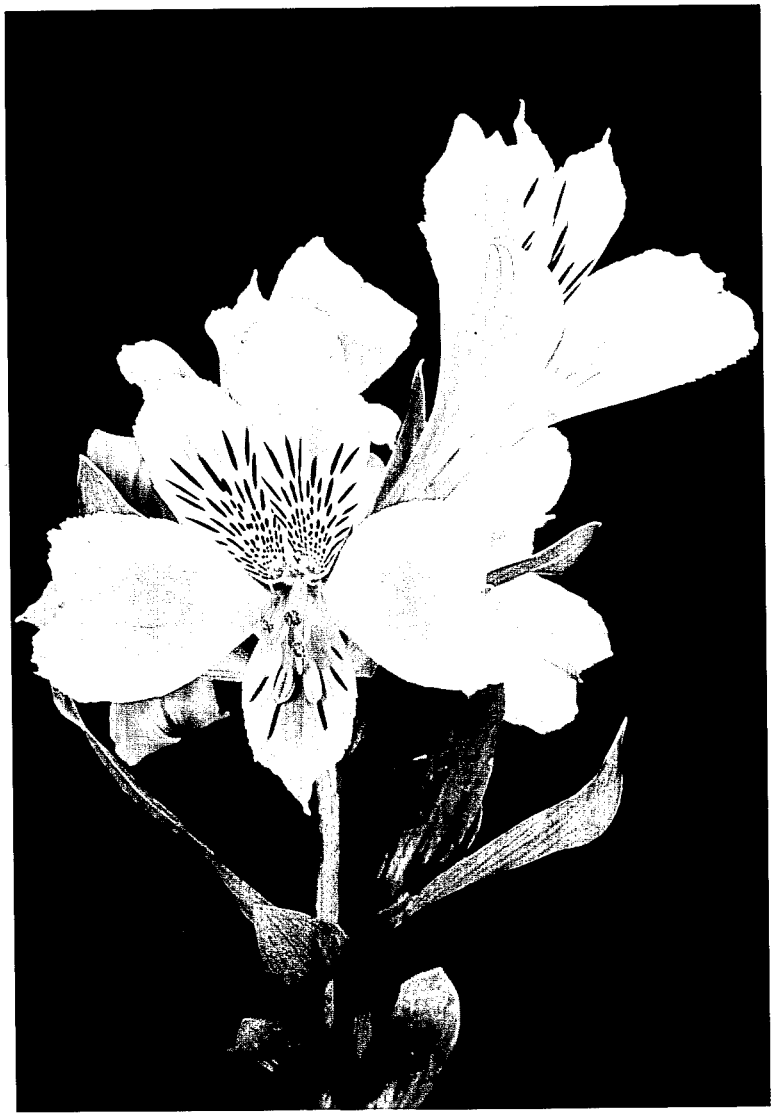

* * * * *